United States Patent [19]

Sauerbaum et al.

[11] Patent Number: 4,877,329
[45] Date of Patent: Oct. 31, 1989

[54] METHOD AND APPARATUS FOR MEASURING THE DEW POINT OF A GAS

[75] Inventors: Thomas Sauerbaum, Gross Grönau; Stefan Kähning, Lübeck, both of Fed. Rep. of Germany

[73] Assignee: Draegerwerk Aktiengesell Schaft, Fed. Rep. of Germany

[21] Appl. No.: 169,409

[22] Filed: Mar. 17, 1988

[30] Foreign Application Priority Data

Mar. 18, 1987 [DE] Fed. Rep. of Germany ....... 3708697

[51] Int. Cl.$^4$ ............................................. G01N 25/68
[52] U.S. Cl. ......................................... 374/28; 374/20
[58] Field of Search ..................... 374/16, 21, 25, 27, 374/28, 20; 338/23, 24, 34, 35; 361/286; 324/61 R

[56] References Cited

U.S. PATENT DOCUMENTS

| 3,552,186 | 1/1971 | Sproul | 374/21 |
| 3,930,398 | 1/1976 | Levina et al. | 374/21 |
| 4,276,768 | 7/1981 | Dadachanji | 374/28 |
| 4,579,462 | 4/1986 | Rall et al. | 374/28 |
| 4,626,774 | 12/1986 | Regtien | 374/28 |

FOREIGN PATENT DOCUMENTS 3446277 6/1986 Fed. Rep. of Germany ........ 374/28

Primary Examiner—William A. Cuchlinski, Jr.
Assistant Examiner—Jeffrey J. Hohenshell
Attorney, Agent, or Firm—McGlew & Tuttle

[57] ABSTRACT

A method for measuring the dew point according to patent application P 36 33 015 is expanded so that an automatic zero point correction can be carried out. For this purpose, the heating power on the heating device is raised to a point, at which the dew evaporates and the sensor-specific property, for example the capacity, is measured and supplied to the evaluating unit as a calibration signal.

4 Claims, 1 Drawing Sheet

METHOD AND APPARATUS FOR MEASURING THE DEW POINT OF A GAS

BACKGROUND OF THE INVENTION

1. Field of the Invention

This invention relates, in general, to devices for measuring characteristics of gases and, in particular, to a new and useful apparatus and method for measuring the dew point of a gas.

A method for measuring the dew point using a sensor and a tempering device having a heater and a cooler, in which a surface of the sensor which is exposed to the atmosphere to be examined is brought through an adjustable tempering by the tempering device to a temperature which leads to the formation of dew on the sensor surface and in response to the formation of the dew, a specific sensor property is changed and the tempering device is regulated to obtain a constant dew layer thickness on the sensor surface, with the sensor temperature detected by a temperature sensor being indicated as the dew point temperature and using the cooler to create a variable degree of cooling in order to draw from the sensor more heat than is required for reaching the dew point temperature, using the heater to provide an additional heating of the sensor surface causing it to reach the dew point temperature, and for purposes of calibration the heating power of the geshichen is raised so far that complete evaporation of the dew occurs, and, upon evaporation of the dew, the specific sensor property is measured and supplied as a calibration signal to the evaluating unit.

For measuring the dew point of a gas, dew point sensors are used, which are kept at such a temperature that formation of dew on the sensor surface occurs. In the process, a specific sensor property is determined, for example, the capacity of a capacitor due to the great dieelectric constant of water, changes as a function of the dew formation. For setting and regulating the sensor temperature to a constant dew layer thickness, a cooling device is used as a tempering device. The temperature of the sensor through the tempering device, at varying vapor contents in the atmosphere, is made to follow continuously the differing dew points at any given time. A temperature sensor measures the temperature of the sensor and diplays it as the dew point temperature (German Pat. No. 32 32 995.) By dividing the tempering device into a separate cooling device and a separate heating device—as described in application No. P 36 33 015—the cooling capacity can be so apportioned so that it draws from the sensor more heat than would be required for reaching the dew point to be expected. In addition, a heating device of lower heating capacity is responsible for a more sensitive and more readily controllable heat supply for achieving the dew point temperature to be determined, and—in this way permits compensating for fluctuations of the dew point rapidly and precisely.

In the course of longer-lasting operation, or following repeated turning on and turning off of equipment operating according to this method, it may happen that particles are deposited on the sensor surface or substances which were dissolved in the condensate and are deposited upon being heated or dried. Depending on the nature of the residues and the extent to which they effect the specific sensor property utilized for taking measurements (for example, its capacity or electrical conductivity) the zero point can gradually become displaced in the course of the measurements without it being noticed and can thus lead to falsification of the measuring results.

SUMMARY OF THE INVENTION

The present invention is an improvement on the method according to patent application P 36 33 015 such that automatic zero point correction can occur.

The advantage of the invention lies primarily in that now either shortly before the beginning of a measuring cyle or while taking measurements, a calibration process can be instituted in shorter or longer sequential time segments. The calibration signal then defines the zero point of the sensor signal for the subsequent measurement of the dew point.

A measuring arrangement for carrying out the method contains the sensor element together with the temperature sensor and a heating device on a common carrier substrate, which is in thermic contact with a cooling device, with the heating device for regulating the heating capacity and the cooling device for permitting cooling being connected to a regulating unit.

The regulating unit transmits for purposes of calibration a control signal for the heating device, through which the heating power is raised so far that complete drying up of the sensor surface occurs. The specific sensor property measured at this time is supplied to the regulating unit as zero point signal and this—together with the subsequent dew point measurements—is processed by the unit.

For measuring the dew point, the sensor element is cooled to a base temperature below the dew point and heated by the heating device until the temperature difference between base temperature and dew point temperature is reached. When this occurs, a dew layer of constant thickness is generated on the surface of the sensor element. If a capacitor is used as a sensor element, this causes a capacity change, which is transmitted as corresponding evaluating signal to the regulating unit. Changes of the dew point and thus changes of the sensor properties are compensated through corresponding increases or decreases of the heating power in the heating device. Through the constant thermal contact with the cooling device following decrease of the heating power, the excess heat quantity of the heating device is immediately diverted, so that in each case a short response time of the sensor element is achieved.

Accordingly, it is an object of the invention to provide a device for measuring the dew point of a gas which comprises a substrate having comb-like interdigitating teeth applied thereon with a sensor having sensor connections on the substrate surrounded by a conducting path having two measuring connections formed as a temperature sensor and including a heating device wound around the temperature sensor having heating connections, a cooling device in contact with the substrate all connected to a regulating unit for determining the cooling and heating power of the heater and cooler and to raise the temperature of the sensor to indicate when the dew point is reached and thereafter to regulate the heater and cooler to maintain a constant temperature on the sensor.

A further object of the invention is to provide a measuring device which is simple in design, rugged in construction and economical to manufacture.

A further object of the invention is to provide a method for measuring the dew point using a sensor and a tempering device having a heater and cooler wherein there is a calibration of the heating power of the heater and the heating is raised so far that complete evaporation of the dew occurs after the gas reaches a dew point at the sensor and upon evaporation of the dew, the specific sensor property is measured and supplied as a calibration signal to an evaluation unit.

The various features of novelty which characterize the invention are pointed with particularity in the claims annexed to and forming a part of this disclosure. For a better understanding of the the invention, its operating advantages and specific objects obtained by its uses, reference is made to the accompanying drawings and descriptive matter in which the preferred embodiments of the invention are illustrated.

BRIEF DESCRIPTION OF THE DRAWINNGS

GENERAL DESCRIPTION OF THE PREFERRED EMBODIMENTS

Figure 1:
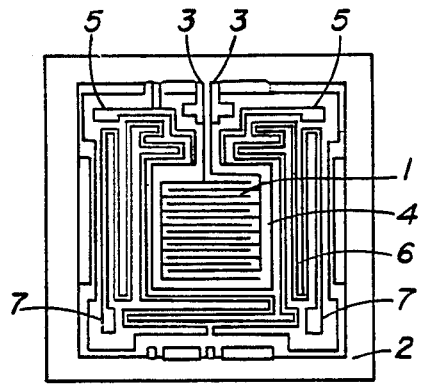
FIG. 1 is a top plan view of a sensor, heating device and temperature sensor for thin film technology constructed in accordance with the invention.

Referring to the drawings, in particular, the invention embodied therein comprises an apparatus and as method for measuring the dew point using a sensor such a sensor 1 and a tempering device having a heater 6 and a cooler or cooling device 8.

In FIG. 1 a sensor 1 is represented, which comprises comb-like interdigitating teeth applied on a carrier or substrate 2. The sensor 1 is equipped with sensor connection 3. The sensor 1 is surrounded at a short distance by a conducting path with two temperature measuring connections formed as a temperature sensor 4. Twisted around the temperature sensor 4 are the conducting paths of a heating device 6 wound around each other, which are provided with heating connections 7. All described lines are applied on the carrier substrate 2 in thin film technology.

Figure 2:
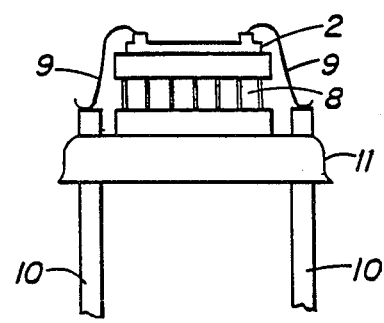
FIG. 2 is a side elevational view of the sensor according to FIG. 1 mounted on a cooling device.

The face of the carrier substrate 2 facing away from the sensor 1 is brought into thermal contact on a cooling device 8 as shown in FIG. 2. The cooling device 8 in this arrangement is developed as a Peltier cooler. The particular connections 3,5,7 of the sensor 1, and the temperature sensor 4 and the heating device 6 are connnected through corresponding connecting wires 9 to associated pins 10 fasted in a base 11.

Figure 3:
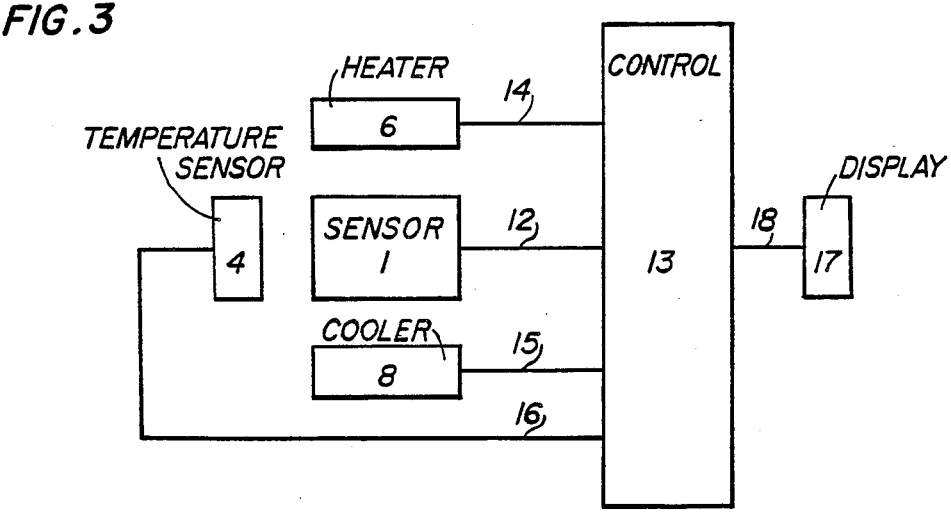
FIG. 3 is a block diagram for a measuring arrangement according to the invention.

The block diagram according to FIG. 3 shows schematically the sensor 1, the sensor connections 3 which are connected via a sensor line 12 to a regulating unit 13. To the regulating unit 13, likewise, the heating device 6 and the cooling device 8 are connected via corresponding heating line 14 and cooling connecting line 15. The temperature sensor 4 is connected to the regulating unit 13 by a temperture measuring line 16. From the regulating unit 13 a connection line 18 leads to a display set 17 for indicating the dew point.

For operating the measuring arrangement, the cooling power of the cooling device 8 is determined by the regulating unit 13 so, that the additionally connected heating device 6, the heating power of which likewise is determined by the regulating unit 13, raises the temperature of the sensor 1 until the sensor 1 transmits across sensor line 12 a signal to the regulating unit 13 indicating that the dew point has been reached. The temperature measured by the temperature sensor 4 here is transmitted over the temperature measuring line 16 to the regulating unit 13 and indicated by the display set 17 as dew point temperature. If, for example, the sensor comprises a planar capacitor, the capacity of which changes instantaneously upon formation of dew, a corresponding signal is transmitted over the sensor line 12 to the regulating unit 13, which immediately maintains the heating power supply to the heating device 6 at a constant level of the current value.

The sensor temperature measured by the temperature sensor 4 is indicated as a dew point temperature by the display set 17. If either the temperature, or the vapor content of the atmosphere to be examined changes, the thickness of the dew layer changes leading to a change in capacity of the sensor. Given those cirumstances, the regulating unit 13 through defined release of heating power to the heating device 6 attempts to restore the thickness of the dew layer to its original, once given thickness.

Due to the low heat capacity of the heating device 6 applied in thin film technology, this regulating process can take place with a very brief time constant. This cools down the sensor 1 by the cooling device 8 as soon as the corresponding heating power of the heating device 6 is lowered. For heating the sensor 1 the heating power of the heating device 6 only needs to be raised correspondingly. In this way, a measuring arrangement is obtained, in which for measuring the dew point temperature a low-power, rapidly reacting temperature regulation takes place within a narrow temperature regulation range of a given base temperature superimposed by the cooling device 8. For purposes of calibration, the regulating unit 13 transmits a control signal to the heating device 6 for heating the sensor surface to the point of completely drying up the layer of dew. Dirt particles—possibly left behind—can be desorbed. If during this heating time, the specific sensor property (capacity or electrical resistance) does not change further, the detected measuring signal is considered to be the zero point calibration value and supplied to the regulating unit 13. On this basis, each subsequent measured value can, for example, be weighed against the stored zero point value.

While specific embodiments of the invention have been shown and described in detail to illustrate the application of the principles of the invention, it will be understood that the invention may be embodied otherwise without departing from such principles.

What is claimed is:

1. A method for measuring the dew point using a unit including a sensor which outputs a signal corresponding to a thickness of a dew layer on a surface exposed to the atmosphere to be examined, and a tempering device connected to the sensor including a heater and a cooler comprising the steps of: cooling and heating the sensor to bring the sensor to a temperature which leads to the formation of a dew layer on the surface of the sensor; detecting the dew layer by measuring the signal of the sensor; measuring the temperature of the sensor as the dew point temperature and calibrating the unit by heating the sensor surface to the point of completely drying the layer of dew, measuring the sensor output and comparing successive measurements of the sensor output to detect a zero rate of change of the sensor output corresponding to a zero point calibration value.

2. A method according to claim 1, further comprising the steps of: detecting changes in the thickness of the dew layer by detecting changes in the sensor signal; restoring the thickness of the dew layer by heating and/or cooling the sensor; and, measuring the temperature of the sensor, upon restoring the thickness of the dew layer, as the new dew point temperature.

3. A method of measuring the dew point using a unit including a sensor outputting a signal representative of a value corresponding to the thickness of a dew layer on a surface of the sensor exposed to the atmosphere to be examined, and a tempering device connected to the sensor including an electric heating unit and a cooling unit in constant contact with said sensor, comprising the steps of: cooling the sensor to a base temperature below the dew point; heating the sensor until the temperature difference between the base temperature and the dew point temperature is reached resulting in a dew layer of constant thickness being generated on the surface of the sensor element; detecting the dew layer by measuring the signal of the sensor; detecting changes in the thickness of the dew layer on the sensor, due to temperature change or change in the vapor contents of the atmosphere; restoring the dew layer on the sensor to its original constant thickness; measuring the temperature of the sensor having a dew layer of constant thickness as the dew point temperature; and, calibrating the unit by heating the sensor surface to the point of completely drying the layer of dew, measuring the sensor output and comparing successive measurements of the sensor output to detect a zero rate of change corresponding to a zero point calibration value.

4. A measurement device for measuring the dew point of a gas, comprising: a substrate, a comb-like formation of a conductor positioned on said substrate forming a sensor, said sensor having a sensor connection on said substrate; a heating device wound around said sensor having heating connections; a cooling device in thermal contact with said substrate; a temperature sensor positioned adjacent said sensor; and regulating means connected to said heating device, connected to said cooling device, connected to said sensor and connected to said temperature sensor for controlling cooling and heating of said sensor by way of said heating device and said cooling device, for receiving an output signal from said sensor representing the thickness of a dew layer on a surface of said sensor and for receiving an output signal from said temperature sensor and calibration means for establishing a zero point calibration value by controlling said heating device to heat the sensor surface to the point of completely drying the layer of dew, and for receiving the sensor output and comparing said successive sensor outputs to detect a zero rate of change in the sensor output corresponding to a zero point calibration value.

* * * * *